United States Patent
Rajamani et al.

(10) Patent No.: US 8,419,652 B2
(45) Date of Patent: Apr. 16, 2013

(54) NON INVASIVE ANALYSIS OF BODY SOUNDS

(75) Inventors: Kumar T. Rajamani, Bangalore (IN);
Nagaraju Bussa, Hyderabad (IN);
Jithendra Vepa, Bangalore (IN);
Abhishek Jain, Madhya Pradesh (IN)

(73) Assignee: Koninklijke Philips Electronics N.V., Eindhoven (NL)

( * ) Notice: Subject to any disclaimer, the term of this patent is extended or adjusted under 35 U.S.C. 154(b) by 202 days.

(21) Appl. No.: 12/920,116

(22) PCT Filed: Mar. 3, 2009

(86) PCT No.: PCT/IB2009/050860
§ 371 (c)(1),
(2), (4) Date: Aug. 30, 2010

(87) PCT Pub. No.: WO2009/109917
PCT Pub. Date: Sep. 11, 2009

(65) Prior Publication Data
US 2011/0009759 A1 Jan. 13, 2011

(30) Foreign Application Priority Data
Mar. 4, 2008 (EP) ..................................... 08305047

(51) Int. Cl.
*A61B 5/08* (2006.01)

(52) U.S. Cl.
USPC .......................................... 600/528; 600/586

(58) Field of Classification Search .................. 600/300, 600/453–464, 508–528, 586
See application file for complete search history.

(56) References Cited

U.S. PATENT DOCUMENTS

| 5,165,417 | A | 11/1992 | Murphy, Jr. | |
| 5,218,969 | A * | 6/1993 | Bredesen et al. | 600/523 |
| 5,844,997 | A | 12/1998 | Murphy, Jr. | |
| 5,871,446 | A | 2/1999 | Wilk | |
| 6,139,505 | A * | 10/2000 | Murphy | 600/532 |
| 6,409,684 | B1 | 6/2002 | Wilk | |
| 6,699,204 | B1 | 3/2004 | Kehyayan et al. | |
| 2002/0183642 | A1 | 12/2002 | Murphy | |
| 2005/0043643 | A1 | 2/2005 | Priemer | |
| 2005/0059896 | A1 * | 3/2005 | Drakulic | 600/509 |
| 2005/0078533 | A1 | 4/2005 | Vyshedskiy et al. | |
| 2006/0056641 | A1 | 3/2006 | Nadjar et al. | |
| 2006/0167385 | A1 | 7/2006 | Guion | |

FOREIGN PATENT DOCUMENTS

| DE | 2004013339 U1 | 10/2004 |
| JP | 01131642 | 5/1989 |
| JP | 3015441 A2 | 1/1991 |
| WO | 2004105612 A1 | 12/2004 |

OTHER PUBLICATIONS

McKee et al: "Sound Localization in the Human Thorax"; IMTC 2005—Instrumentation and Measurement Technology Conference, Ottawa, Canada, May 2005, pp. 117-122.
"Cardiovascular"; No Author, Article on Symptoms of Heart Disease, pp. 199-209.
O'Grady et al: "Clinical Cardiology Concepts for the Dog and Cat"; 28 Page Article on the Clinical Evaluation of Heart Disease, Downloaded From HTTP:/WWW.VETGO.COM/CARDIO/CONCEPTS/CONCSECT.PHP?CONCEPTKEY=49, on Mar. 11, 2008.

* cited by examiner

*Primary Examiner* — Scott Getzow

(57) ABSTRACT

This method for analysing the sounds of body fluid flows includes:—simultaneously acquiring (2) sounds from various locations of a body;—identifying (6) the points of maximum sound intensity (PMIs) of the acquired sounds for each acquisition instant;—determining (10) the source locations of the acquired sounds; and—determining (12, 14) the sound radiation patterns of the acquired sounds. A corresponding device, system and program perform this method.

18 Claims, 2 Drawing Sheets

NON INVASIVE ANALYSIS OF BODY SOUNDS

FIELD OF THE INVENTION

The present invention concerns a method, a device and a system for analysing the sounds of body fluid flows.

In several organs of bodies, such as the human body, the fluid flows have distinctive sounds characteristics and the knowledge of those sounds characteristics provides important information to physicians for establishing diagnosis.

For example, heart murmurs or abnormal heart sounds are caused by turbulent blood flow through narrow or abnormally functioning valves.

BACKGROUND OF THE INVENTION

Several existing techniques allow to acquire sounds from various locations of the body and to analyse them. This is the case for example in the patent document U.S. Pat. No. 6,699,204-B1

However, the existing techniques focus on identifying the location of the origins of sound but fail to analyse other important distinctive characteristics.

More precisely, an important sound characteristic is the radiation of the sounds. To illustrate, a murmur of aortic stenosis would originate in the second interspace on the right of the sternum and may radiate to the carotid arteries. A murmur of mitral valve prolapse may radiate into the left axilla.

Today, the physicians must identify the sound radiation by manual auscultation using stethoscopes. Identifying the sound radiations is time consuming, leaves no medical record and depends essentially on the abilities and skills of the physician.

Accordingly, there is a need for a technique that would allow a better analysis of the sounds of the body fluid flows.

SUMMARY OF THE INVENTION

To solve this problem, the invention relates to a method for analysing the sounds of body fluid flows comprising simultaneously acquiring sounds from various locations of a body and determining characteristics of the fluid flows wherein determining characteristics comprises identifying the points of maximum sound intensity of the acquired sounds for each acquisition instant determining the source locations of the acquired sounds, and determining the sound radiation patterns of the acquired sounds.

The invention also relates to a device for analysing the sound of body fluid flows comprising an input unit for receiving data corresponding to sounds simultaneously acquired from various locations of a body and an analysing unit for determining fluid flows characteristics wherein said analysing unit comprises means for identifying the points of maximum sound intensity for each acquisition instant, means for determining the source locations of the acquired sounds, and means for determining the sounds radiation patterns of the acquired sounds.

The invention also relates to a computer program performing said method and to a system including said device.

The invention provides a non invasive solution to analyse characteristics of the body fluid flows in more detail than the existing solutions and especially the sound radiation pattern.

BRIEF DESCRIPTION OF THE DRAWINGS

Those and other features and advantages of the invention will become apparent upon reading the following description given only by the way of non limiting example, and offered with reference to the annexed figures in which.

DETAILED DESCRIPTION OF THE INVENTION

The embodiment of the example relates to the acquisition of acoustic heart signals from the entire chest region of a human body, that is to say the analysis of the chest sounds.

Figure 1:
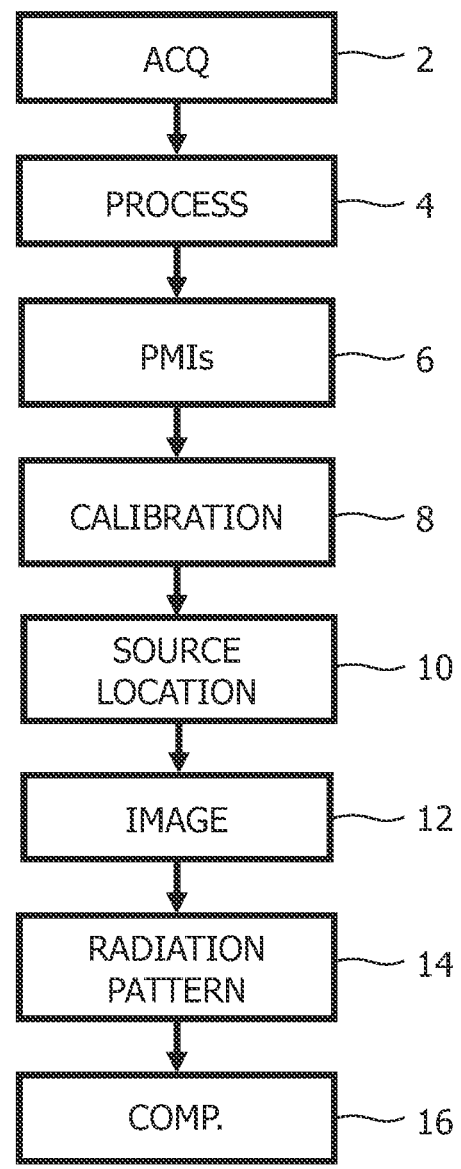
FIG. 1 represents a general flow chart of the process of the invention.

The method of the invention will now described with reference to FIG. 1.

The method starts by a simultaneous acquisition 2 of the sounds of body flows by an adapted array of sensors set on specific monitored areas of the body. For each acquisition instant, the sound level for each sensor is recorded.

The acquisition is followed by a processing step 4 during which the acquired signals are transformed in order to provide digital signals corresponding to the acquired sounds. In the described example, the output of the processing step is a table referencing the characteristics of the acquired sound for each sensor and for each acquisition instant.

Acquisition and processing of acoustic signals for body fluid flows is a well documented technique and will not be described in details.

The method then comprises identifying 6 the locations of the maximum sound intensity for each acquisition instant. Accordingly, through the array of sensors, a mapping of the locations of the points of maximal intensity (PMIs) is obtained for each acquisition instant.

Advantageously, the method comprises a calibration 8 during which radiation flows cycles and body regions are defined.

More precisely, in certain cases, such as for blood flows, body fluid flows present cyclic patterns. This is detected during the calibration by analysing several acquisition instants and identifying said cycles.

Similarly, body regions can be defined by the analysis of several acquisition instants by considering the repetitions of the PMIs. In the described example of heart sounds monitoring, four primary regions of acquisition are defined, namely the aortic area, the pulmonic area, the mitral area and the tricuspid area.

The method then comprises determining 10 the locations of the sound sources. This sources locations determination is performed by processing several acquisition instants and the location of the maximum of several PMIs is determined as a source location.

Advantageously, a source location is determined for each body region.

From a practical point of view, in the embodiment described, the calibration and the determination of the source locations are performed simultaneously by use of a loop classification algorithm applied to the PMIs and converging over several acquisition instants.

The process then comprises creating 12 an instantaneous sound record with the source locations and the points of maximal intensity.

In the embodiment described, this record is formed as a digital image, also called snapshot or frame, graphically representing the source locations of the sounds and the points of maximal intensity. Advantageously other sound characteristics such as frequency, amplitude, duration or the like are also part of this image.

The method then comprises determining 14 the radiation pattern for the acquired sounds. In the embodiment described, this is performed by applying a tracking algorithm between consecutive images. Each image containing a distribution of the intensity of sounds, the processor computes how and where the sounds of each source radiate using image tracking algorithms applied to the PMIs associated with that source.

Advantageously, the heuristic that the acoustic signals usually radiate in particular patterns is used to refine and guide the tracking system to determine the radiation pattern of the acquired sounds. Reference radiation patterns are used to improve the determination.

At that stage, the process of the invention is able to provide both an instantaneous view of the source locations and points of maximum sound intensity as well as radiation patterns tracked over several consecutive images. In the embodiment described those elements are graphically provided to a physician through a display screen.

In the embodiment described, the method of the invention also comprises comparing 16 the acquired sounds and determined radiation patterns to references in an attempt to match the acquired sounds and radiation patterns to existing conditions. For example, the output of the comparison system is a correlation percentage identifying the match between the characteristics of the acquired sounds and the references.

The comparison allows a categorization of the etiology of the radiation by comparing its location, timing, duration and other characteristics to existing references.

This comparison provides a physician with a helpful insight on the diagnosis and assists the physician or the operator in the decision process. Furthermore, the information obtained does not depend upon the skills or abilities of the operator or of the physician and can be recorded for later use.

Accordingly, the invention describes a non invasive method for analysing the radiation patterns of body fluid flows and providing help for the diagnosis of medical conditions.

Figure 2:
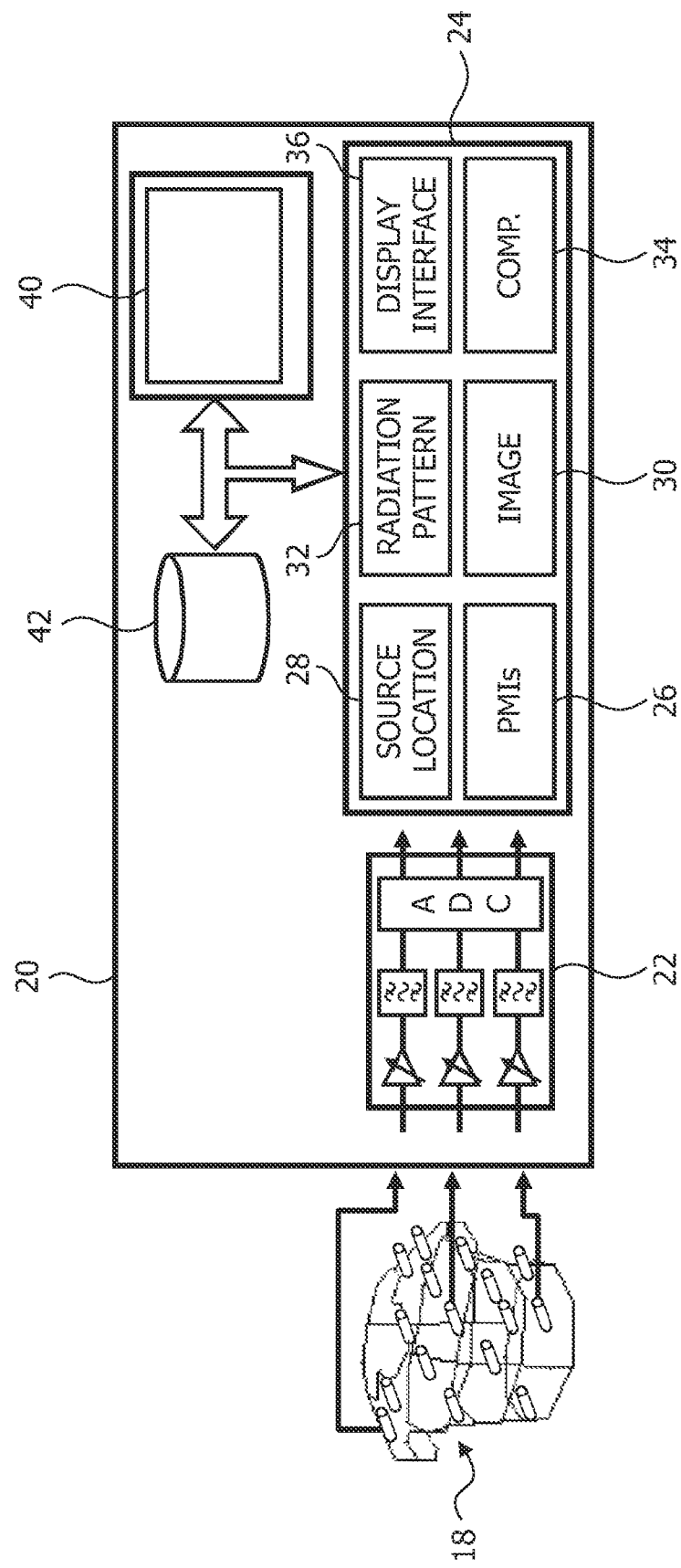
FIG. 2 represents a schematic of the system of the invention.

With reference to FIG. 2, a system according to an embodiment of the invention is now described.

The system first comprises a sensor assembly 18 comprising an array of sound sensors which are, in the example, set on an inflatable wearable vest. The inflatable vest also comprises pressure means which are not represented. Those pressure means are used to apply, through the inflatable vest, a similar pressure to each sensor and to press the sensors towards the chest of the human body.

For example, the sensors are microphones or piezo-electric sensors. The distribution of the sensors is arranged so that the entire chest region is optimally covered.

The sensor assembly 18 performs the simultaneous acquisition 2 of sounds from the body fluid flows as described previously with reference to FIG. 1. The sensor assembly 18 is connected to an analysing apparatus 20 which, in the example, is a dedicated device. In another embodiment, this analysing apparatus can be implemented as a mix of software and hardware in another electronic apparatus, such as for example a computer.

The analysing apparatus 20 first comprises an input stage 22 with appropriate amplifiers, band-pass filters, and analog to digital converters. Of course, the input stage 22 is adapted to the actual sensors used in the sensor assembly 18. The input stage 22 performs the processing step 4 as described with reference to FIG. 1.

The digital signals corresponding to the acquired sounds are then analysed by a processor 24.

The processor 24 first comprises a unit 26 for determining the points of maximum sound intensity or PMIs, as described with reference to step 6 of FIG. 1. The processor 24 also comprises a unit 28 for determining the locations of the sources of the acquired sounds. As indicated with reference to FIG. 1, in the embodiment described, the calibration 8 is performed through a converging determination 10 of the source locations. Accordingly, unit 28 performs both steps 8 and 10 as described with reference to FIG. 1.

The output of units 28 and 26 are provided to an image determination unit 30. As described with reference to step 12, this image determination unit 30 provides digital images featuring the source locations of the sounds and the points of maximum sound intensity to a radiation pattern determination unit 32. The radiation pattern determination unit 32 performs the determination step 14 by tracking the points of maximum sound intensity for each source location over several frames.

Advantageously, the processor 24 also comprises a pattern comparing unit 34 for performing the comparison step 16 as described with reference to FIG. 1.

Finally, in the described example, the processor 24 also comprises a display interface 36 for controlling a display screen 40 and displaying the frames, the radiation patterns and the results of the comparing unit to a physician or an operator.

Generally speaking the processor 24 is also connected to a memory unit 42 for storing the acquired sounds, the image data, the radiation patterns and any other final or intermediate result.

Of course many other embodiments of this system can be realized and the sensors, input stage, processing units, memory and display can be spread over several apparatus or combined.

In one embodiment, the sensors are digital wireless sensors connected to a wireless computer running a software program and using the computer screen and memory unit.

In such an embodiment, the method described above is performed by a computer program comprising instructions which are executed by a processor of a computer. This program is formed on a computer software medium.

In another embodiment, the sensors transmit their data to the processor through a telecommunication network such as the Internet to allow remote monitoring.

Of course, the invention can be used for other bodies than the human body and other fluid flows than the blood flows.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for analysing the sounds of body fluid flows comprising:
    repeatedly and simultaneously acquiring sounds from a plurality of locations of a body with a plurality of acoustic sensors distributed on the body; and
    with a processor, determining characteristics of the body fluid flows, including:
        identifying points of the maximum sound intensity (PMIs) of the acquired sounds for each of a plurality of sound acquisitions;
        determining source locations of the acquired sounds; and
        determining sound radiation patterns of the acquired sounds.

2. The method according to claim 1, wherein determining the source locations of the acquired sounds comprises analysing several acquisition instants and determining the maximum of several points of maximum sound intensity as a source location.

3. The method according to claim 2, further comprising:
with the processors, defining sound acquisition cycles and/or regions based on a periodicity and repetition of the points of maximum sound intensity.

4. The method according to claim 1, further comprising:
with the processor, comparing the determined fluid flow characteristics with existing reference flow characteristics and providing a match likelihood of the characteristics of the acquired sounds with said existing reference flow characteristics.

5. The method according to claim 1, wherein said body fluid flows are human heart blood flows.

6. The method according to claim 1, further including:
on a display, displaying an image depicting the points of maximum sound intensity of the sounds acquired from the body.

7. The method according to claim 1, further including:
on a display, displaying image frames depicting the identified points of maximum sound intensity, the determined source locations, and the determined sound radiation patterns.

8. The method according to claim 1, further including:
forming a plurality of digital image frames, each digital image frame being formed from the determined source locations and the identified points of maximum sound intensity for each of the plurality of simultaneously acquired sound acquisitions.

9. The method according to claim 8, further including:
determining the sound radiation patterns from the plurality of digital image frames.

10. A processor programmed to perform the method according to claim 1.

11. A method for analyzing the sounds of body fluid flows comprising simultaneously acquiring sounds from a plurality of locations of a body with an acoustic transducer and determining characteristics of the body fluid flows, wherein determining the characteristics of the fluid flows comprises, with a processor:
identifying the points of maximum sound intensity (PMIs) at eascsh of a plurality of times that the sounds are acquired;
determining source locations of the acquired sounds;
creating a digital image mapping the points of maximum sound intensity each time the sounds are acquired;
tracking the points of maximum sound intensity over a consecutive plurality of the images to obtain patterns indicative of the acquired sounds radiating through the body.

12. The method according to claim 11, wherein tracking the points of maximum sound intensity further comprises refining the acquired sound radiation patterns using reference sound radiation patterns.

13. The method according to claim 11, further including:
on a display device, displaying an image depicting at least one of the source locations of the acquired sounds, the points of maximum sound intensity of the acquired sounds, and the patterns of the acquired sounds radiating through the body.

14. A system for analysing sounds of body fluid flows comprising:
an input unit which receives electronic data corresponding to sounds simultaneously and repeatedly acquired from a plurality of locations of a body with a plurality of acoustic sensors; and
a processor for determining fluid flows characteristics, the processor being programmed to:
identify points of maximum sound intensity (PMIs) for each of a plurality of the simultaneously acquired sound acquisitions;
determine source locations of the acquired sounds from the identified points of maximum sound intensity identified over the plurality of sound acquisitions;
form a plurality of digital image frames, each digital image frame being formed from the determined source locations and the identified points of maximum sound intensity for each of the plurality of simultaneously acquired sound acquisitions; and
determine sound radiation patterns of the acquired sounds from the digital image frames.

15. The system for analysing sounds of body fluid flows according to claim 14 further including:
a sensor assembly which simultaneously acquires the sounds at the plurality of locations of the body.

16. The system according to claim 15, wherein said sensor assembly includes the plurality of acoustic sensors mounted on an inflatable wearable vest for a human body.

17. The system according to claim 14, further including:
a display device which displays the plurality of digital frames.

18. A non-transitory computer-readable medium carrying a set of instructions which control a processor to perform the steps of the method as claimed in claim 1.

* * * * *